(12) United States Patent
Harre et al.

(10) Patent No.: US 8,579,497 B2
(45) Date of Patent: Nov. 12, 2013

(54) DEVICE, MIXER AND SYSTEM FOR MIXING AND DISPENSING OF A MATERIAL AND METHOD OF USE

(75) Inventors: Manfred Harre, Landsberg am Lech (DE); Dirk Müller-Paul, Neubeuern (DE)

(73) Assignee: 3M Innovative Properties Company, St. Paul, MN (US)

( * ) Notice: Subject to any disclaimer, the term of this patent is extended or adjusted under 35 U.S.C. 154(b) by 719 days.

(21) Appl. No.: 12/281,999

(22) PCT Filed: Mar. 8, 2007

(86) PCT No.: PCT/US2007/063526
§ 371 (c)(1),
(2), (4) Date: Jun. 15, 2009

(87) PCT Pub. No.: WO2007/106701
PCT Pub. Date: Sep. 26, 2007

(65) Prior Publication Data
US 2009/0279382 A1      Nov. 12, 2009

(30) Foreign Application Priority Data
Mar. 10, 2006  (EP) .................................. 06004960

(51) Int. Cl.
*B01F 7/00*  (2006.01)
*B67D 7/74*  (2010.01)

(52) U.S. Cl.
USPC ...................... 366/331; 366/172.1; 222/145.6

(58) Field of Classification Search
USPC .......... 366/171.1, 172.1–173.2, 176.1, 181.5, 366/189, 331; 403/359.1, 359.3, 359.4, 403/359.6, 360, 24; 222/145.5, 145.6, 222/325–327

See application file for complete search history.

(56) References Cited

U.S. PATENT DOCUMENTS

| 2,833,576 | A | * | 5/1958 | Cirone .......................... 403/334 |
| 2,869,907 | A | * | 1/1959 | Deliso ........................ 403/359.6 |
| 2,893,769 | A | * | 7/1959 | Deliso ........................ 403/359.6 |
| 3,290,918 | A | * | 12/1966 | Weasler .......................... 72/340 |
| 3,485,520 | A | * | 12/1969 | Alexander .................... 403/334 |
| 4,185,388 | A | * | 1/1980 | Jarby ............................. 433/125 |
| 4,212,546 | A | | 7/1980 | Porteous |
| 4,832,573 | A | * | 5/1989 | Dorski ..................... 416/241 A |
| 4,832,637 | A | * | 5/1989 | Goluba .......................... 440/83 |
| 5,249,862 | A | | 10/1993 | Herold et al. |
| 5,366,286 | A | * | 11/1994 | Ruttimann .................... 366/129 |
| 5,402,710 | A | * | 4/1995 | Chen ................................ 99/348 |
| 6,439,760 | B1 | * | 8/2002 | Langeloh et al. ............. 366/206 |
| 6,443,612 | B1 | * | 9/2002 | Keller ........................... 366/307 |

(Continued)

FOREIGN PATENT DOCUMENTS

DE  32 33 366       9/1983
DE  297 05 741 U   8/1998

(Continued)

*Primary Examiner* — Charles E Cooley

(57) ABSTRACT

A device for mixing and dispensing dental materials is provided, comprising a drive shaft for driving a mixer. The mixer is placeable on the drive shaft in a first and a second position, wherein in the first position a guiding section of the drive shaft is mated with an engagement section of the mixer, but an engagement section of the drive shaft is not engaged with the engagement section of the mixer, and in the second position the engagement section of the drive shaft is also engaged with the engagement section of the mixer.

17 Claims, 5 Drawing Sheets

(56) References Cited

U.S. PATENT DOCUMENTS

| | | | |
|---|---|---|---|
| 7,387,462 B2* | 6/2008 | Hacker | 403/359.6 |
| 8,147,122 B2* | 4/2012 | Pieroni | 366/171.1 |
| 8,322,909 B2* | 12/2012 | Gramann et al. | 366/172.2 |
| 8,371,744 B2* | 2/2013 | Walter et al. | 366/331 |
| 2002/0175186 A1* | 11/2002 | Keller | 222/145.6 |
| 2003/0123323 A1 | 7/2003 | Bublewitz et al. | |
| 2004/0257909 A1* | 12/2004 | Pieroni | 366/172.1 |
| 2009/0279382 A1* | 11/2009 | Harre et al. | 366/133 |
| 2012/0097702 A1* | 4/2012 | Harre et al. | 222/1 |
| 2012/0148980 A1* | 6/2012 | Gramann | 433/90 |
| 2012/0218856 A1* | 8/2012 | Walter et al. | 366/307 |

FOREIGN PATENT DOCUMENTS

| | | |
|---|---|---|
| EP | 1 149 627 | 10/2001 |
| EP | 1 602 342 | 12/2005 |
| WO | WO 02/21652 | 3/2002 |

* cited by examiner

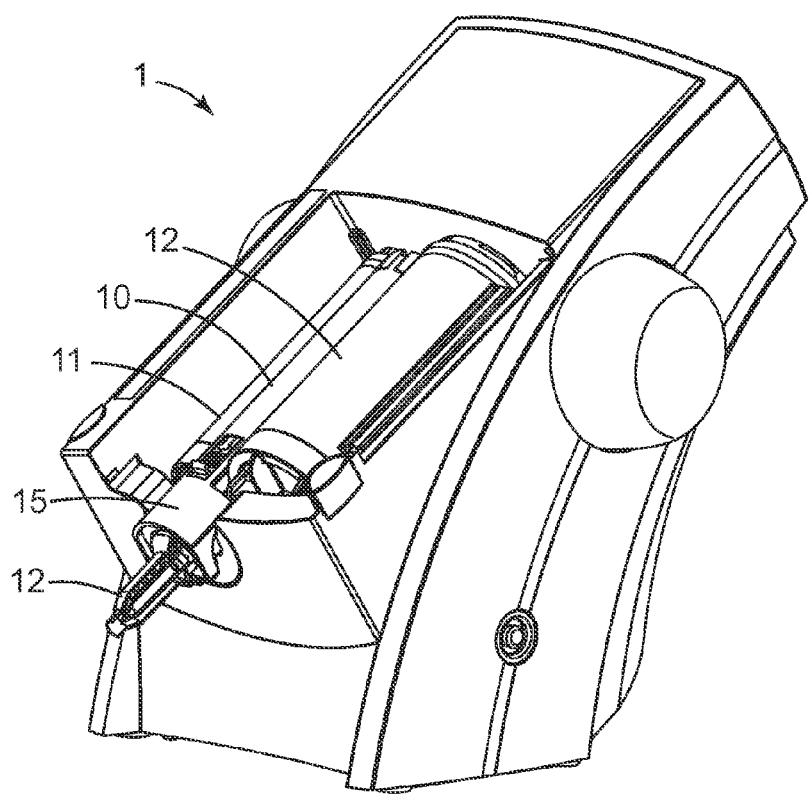
FIG. 1
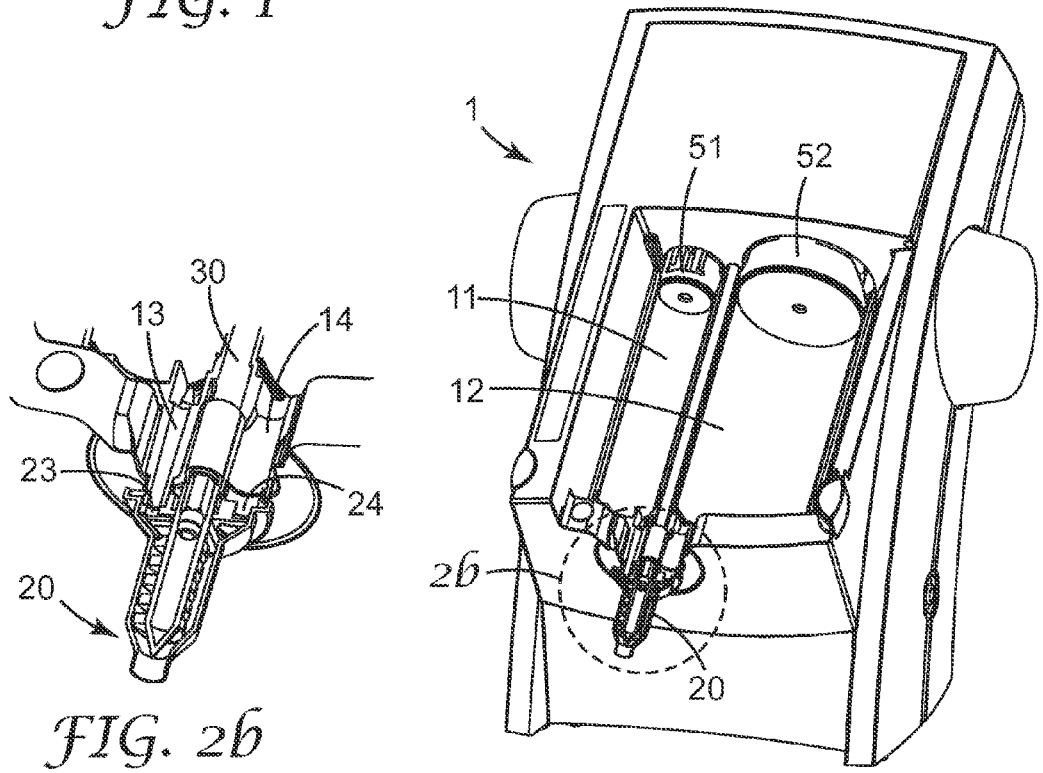
FIG. 2b
FIG. 2a

DEVICE, MIXER AND SYSTEM FOR MIXING AND DISPENSING OF A MATERIAL AND METHOD OF USE

CROSS REFERENCE TO RELATED APPLICATIONS

This application is a national stage filing under 35 U.S.C. 371 of PCT/US2007/063526, filed Mar. 8, 2007 which claims priority to European Application No. 06004960.8, filed Mar. 10, 2006, the disclosure of which is incorporated by reference in their entirety herein.

FIELD OF THE INVENTION

The present invention relates to a device for mixing and dispensing dental materials, such as dental impression materials. The present invention also relates to a dynamic mixer for use with a device for mixing and dispensing dental materials, and a system including a device and a mixer. The invention is also directed to a method of mounting a mixer to a device, and to driving such a mixer.

BACKGROUND OF THE INVENTION

Pasty multi-component materials, such as dental impression materials, are often stored separately from each other as individual components, because once the components come into contact with each other a chemical reaction is initiated that eventually turns the mixed composition into a hardened mass. For that reason, such materials are widely available in packages that include two compartments or two separate containers that keep the components initially isolated from each other.

Dental materials as mentioned are generally mixed together shortly prior to use in the dental practice by the dentist or the dentist's assistant. In recent years, devices have been developed which provide for the automatic mixing and dispensing dental impression materials, which provide high precision with regard to the ratio of the two components to be mixed, and the homogeneity of the mixture. The dental impression material components are simultaneously supplied from separate material chambers to a mixer, which mixes and dispenses the mixed paste from a front end. The mixer may be a static mixer (meaning that the structures that cause mixing do not move relative to the mixing chamber) or a dynamic mixer (meaning that the structures that cause mixing do move relative to the mixing chamber, normally in a rotary manner). The paste exiting from the front end of the mixer may be supplied directly onto a dental impression tray that can be placed in a patient's mouth. When the mixed components harden, the tray is removed and the hardened impression material provides an impression of the patient's teeth.

Once the material components have come into contact with each other, normally near or within the mixing chamber, the material in the mixing chamber can only be stored for a relatively short time because the mixed material will soon harden inside the mixing chamber if it is not dispensed and used. Therefore mixers used with such devices generally can only be used once, and are therefore generally exchangeable and often disposable parts. Dentists and their assistants may have to remove and replace mixers several times each day.

Examples of dynamic mixers are found in, e.g., WO 00/21652, EP-A-1 149 627, U.S. Pat. No. 5,249,862 or DE-U-297 05 741. These known dynamic mixers have at their rear end (the inlet side) a central opening for coupling to a drive shaft of a motorized mixing and dispensing device, and two additional inlet connectors for receiving the material components which are to be mixed. The central opening has a hexagonal cross-section for engagement with a corresponding drive shaft also having a hexagonal cross-section, which enables the motor of the mixing and dispensing device to rotate a mixing rotor having mixing paddles.

To ensure proper mixing and dispensing, the mixer has to be coupled correctly to the drive shaft of the device and the connectors for the material components. If the mixer is improperly coupled to the drive shaft, the motor will not be able to drive the mixing rotor correctly, resulting in unmixed or poorly mixed material components. If the connectors for the material components are improperly aligned and connected, material components can escape from the mixer and make a really big mess. With a device for mixing and dispensing two-component materials, a three-way-coupling is thus provided at the device, comprising two material connectors and the drive shaft, which has to be combined with corresponding parts of the mixer. The connectors and the drive shaft are linearly arranged side by side, with the drive shaft located in the middle.

Because the drive shaft, with its hexagonal cross-sectional shape, is oriented by random, coupling of the mixer to the device normally requires a two-step process. First, the user orients the drive-shaft opening of the mixer with respect to the orientation of the drive shaft, and places the mixer at least partly onto the drive shaft without regard to whether the material component connectors are aligned. Then the user aligns the component connectors on the mixer with the corresponding connectors on the device, and finishes connecting the mixer to the device. The drive shaft and the material component connectors are thus all aligned and connected, and the device should operate as expected. However, because the mixer is often attached to the dispenser quickly, the two may not be properly engaged or seated, resulting in unsatisfactory performance.

SUMMARY OF THE INVENTION

The present invention in a first aspect is related to an improved device for mixing and dispensing multi-component materials, such as dental impression materials. According to a preferred embodiment, the present invention relates to a device for mixing and dispensing dental impression material, comprising a drive shaft for driving a mixer, wherein the mixer can be placed on the drive shaft in a first and a second position. In the first position a guiding section of the drive shaft is mated with an engagement section of the mixer, but an engagement section of the drive shaft is not engaged with the engagement section of the mixer, and in the second position the engagement section of the drive shaft is also engaged with the engagement section of the mixer. In other words, when the mixer is placed on the drive shaft in the first position a loose fit, force-fit or frictional connection is provided, while when the mixer is placed on the drive shaft in the second position a positive engagement between the mixer and the drive shaft is created.

Preferably the first position further represents a position in which a guiding section of the drive shaft is mated or associated with the engagement section of the mixer, meaning that the mixer placed on the drive shaft in its first position is preferably axially guided with radial restraint by the drive shaft but the engagement sections of the mixer and the drive shaft are disengaged. In contrast, when the mixer is placed on the drive shaft in its second position, i.e. after it has been further pushed or moved towards the device, the engagement sections are engaged and transmission of torque from the drive shaft to the mixer is enabled. In this context it is pointed out that the transmittable torque is preferably sufficient for mixing the material when the mixer is placed on the drive shaft in its second position, while when the mixer is placed on the drive shaft in its first position the transmittable torque is lower.

The term "guiding section" encompasses structures serving as radial restraint providing axial guidance of a counterpart mated with the guiding section but rotatability between the mated parts. Preferably the guiding section allows guided axial movement of a counterpart over a length of the guiding section, preferably a length of at least 2 mm, and more preferably over a length of 3.5 mm of the guiding section.

Thus, the invention allows the mixer to be initially placed on the drive shaft in a first position without the need of aligning the engagement sections, for example sections with hexagonal cross-sectional shapes, for mating with each other.

In a preferred embodiment of the invention the drive shaft has a front end comprising the guiding section and just to the rear of it separately the engagement section for engagement with the mating engagement section of the mixer. Thus, the engagement section of the mixer in a first position can be placed on the guiding section of the drive shaft. To engage the engagement section of the mixer with the engagement section of the drive shaft the mixer can be moved further towards the rear end on the drive shaft (which is a direction towards the device).

In a further preferred embodiment, the guiding section is adapted such that, when the mixer is placed on the drive shaft in its first position the guiding section is freely rotatable around its longitudinal axis relative to the engagement section of the mixer. Preferably the guiding section of the drive shaft and the engagement section of the mixer form a loose fit or a force-fit, in any case providing free rotatability of both, the guiding section of the drive shaft and the engagement section of the mixer, relative to each other. In this context the terms loose fit and force-fit encompass also a transition fit and a fit providing for very low play between the mating parts but permitting axial guiding with radial restraint of one another.

In another preferred embodiment, the guiding section has a generally circular cross-section. For example the guiding section may comprise cylindrical and/or conical shapes. Preferably the guiding section is of a generally cylindrical shape having a conical section at its front most end (which is the end corresponding to the front end of the drive shaft). Preferably the largest diameter of the guiding section is equal to or less than the smallest width of the engagement section of the mixer, in case the guiding section is the male part and the engagement section of the mixer is the female part. Preferably the dimensions of the guiding section and the corresponding width of the engagement section are in a range of 4 to 6 mm. Preferably the largest diameter of the guiding section is 5 mm and the smallest width of the engagement section is also 5 mm so that preferably a transition fit is provided. The length of guiding section is preferably approximately 5 mm and the length of the engagement section of the driveshaft is preferably approximately 10 mm. The transmittable torque between the drive shaft and the mixer having hexagonal engagement sections is approximately 1.5 Nm, when the engagement section of the drive shaft engages with the engagement section of the mixer. Such a torque can be transmitted when the engagements sections are mated properly, meaning when the engagement section of the mixer is engaged over its full length with the engagement section of the drive shaft.

In an alternate embodiment, the guiding section comprises a non-circular cross-section, for example a generally polygon-shaped cross-section. Preferably such a polygon-shaped cross-section is one of the shapes selected from among a square, a rectangle, a hexagon, a cross and a star.

Preferably such a guiding section is adapted to engage with a mating second engagement section of the mixer. A so formed guiding section engaging with a second, additional engagement section of the mixer may allow for transmitting higher torque relative to a mating with only one engagement section at each mating part.

In a preferred embodiment of the present invention the engagement section of the drive shaft comprises a non-circular cross-section, preferably a hexagonal cross-section. Optionally both, the engagement section and the guiding section of the drive shaft, have generally polygon shaped cross-sections, and the polygon of the guiding section has at least one more side or flat than that of the engagement section of the drive shaft. In a preferred embodiment the engagement section of the drive shaft comprises a female hexagonal cross-section and the guiding section comprises a male star shaped cross-section. With such a configuration the guiding section still provides axial guiding with radial restraint with respect to the hexagonal counters-structure as well as rotatability between the mating parts, because the outer periphery of star shape guides the flats of the hexagonal shape.

In a further optional embodiment the engagement section of the drive shaft comprises a spline or a plurality of splines. This encompasses also a drive shaft comprising any kind of splines or detents which allow for engagement with a structure of the mixer and transmission of a torque. Such splines or detents may be integrally formed or separate parts.

Preferably the drive shaft comprises the male part of the mating of the corresponding engagement sections of the drive shaft and the mixer. Alternatively the drive shaft comprises the female part of the mating of the corresponding engagement sections of the drive shaft and the mixer.

According to another embodiment the drive shaft further comprises a socket that is preferably arranged concentrically around at least a part of the engagement section of the drive shaft. The socket is preferably arranged at the rear end of the engagement section of the drive shaft (which is the end of the engagement section further remote from the front end of the drive shaft). The socket is preferably formed as a rim, collar or flange concentrically arranged on the drive shaft comprising a recess extending axially from the front face of the flange toward the rear end of the drive shaft. Preferably the recess has an outer circular cross-section and the inner cross-section corresponds to the outer size and shape of the mixing shaft (in case the mixing shaft comprises the male part of the mating engagement sections). In an optional embodiment the outer cross-section of the recess is non-circular, for example has a shape as mentioned above for the engagement/guiding sections providing for engagement with a third mating engagement section at the mixer.

In a preferred embodiment the device of the present invention further comprises a chamber for storing a component of the dental impression material, wherein the chamber opens into an outlet which is connectable with a corresponding inlet of the mixer, when the mixer is placed on the drive shaft in its second position. Such a chamber could for example be a foil bag provided exchangeably within a cartridge, wherein the foil bag has a cap with the outlets. Preferably the device further comprises a plunger for expelling the component from the chamber into the mixer, so as to mix and dispense the dental impression material.

Preferably the device of the present invention comprises at least two chambers for storing components of the dental impression material and at least two plungers for expelling the components from the chambers into the mixer, so as to mix and dispense the dental impression material.

Preferably each chamber opens into an outlet and the individual outlets are connectable with corresponding inlets of the mixer, when the mixer is placed on the drive shaft in its second position. Preferably the outlet(s) is/are at least partially connectable with (a) corresponding inlet(s) of a mixer when the mixer is placed on the mixing shaft in its first position. With this configuration placement of the mixer on the drive shaft and connecting it to the outlets is facilitated, because a user of the device can place the mixer on the drive shaft in a first position without taking care of the angular orientation of the engagement sections of the mating parts relative to each other, as required in the prior art. Once the mixer is placed on the guiding section it is easy to connect the inlets of the mixer to the outlets of the chambers because the mixer then is already supported in two dimensions. Thus, the inlets can be aligned to the outlets by just rotating the mixer to the appropriate angular orientation.

According to a another aspect of the present invention a mixer for mixing dental impression material is provided for use with a device for mixing and dispensing of dental impression material. In contrast to the drive shaft of the invention, now the mixer preferably has a guiding section and separate therefrom an engagement section. According to a preferred embodiment the mixer has a front end and an opposite rear end. The rear end comprises the guiding section for mating with an engagement section of the drive shaft and just to the front of the guiding section the engagement section for engagement with the engagement section of the drive shaft.

The mixer according to a preferred embodiment is placeable on the drive shaft of the device for mixing and dispensing dental impression material in a first and a second position, wherein in the first position the guiding section of the mixer is mated with the engagement section of the drive shaft, but the engagement section of the mixer is not engaged with the engagement section of the drive shaft, and in the second position the engagement section of the mixer is also engaged with the engagement section of the drive shaft.

In a preferred embodiment of the invention the cross-section of the engagement section of the mixer comprises a polygon shape. Preferably the cross-section of the engagement section of the mixer comprises a shape selected from among a square, a rectangle, a hexagon, a cross and a star. Further it is preferred that the engagement section of the mixer comprises a cross-section generally corresponding to the cross-sectional shape of the engagement section of the drive shaft. Alternatively the mixer comprises an engagement section having a substantially different cross-section relative to the cross-sectional shape of the engagement section of the drive shaft.

A device having a drive shaft according to the invention is advantageous because it is generally compatible to conventional mixers as commercially available. Thus, such a device provides the advantages of the invention to a variety of mixers available on the market. In contrast, a mixer of the invention is advantageous because it can be used with devices that are already in use on the market.

In an alternate embodiment of the invention the mixer further comprises a second engagement section for engagement with the guiding section of the drive shaft. Preferably the cross-sectional shape of such a second engagement section of the mixer corresponds to a non-circular shaped guiding section of the drive shaft as mentioned above. A second engagement section as mentioned preferably is adapted to allow transmission of a torque from the drive shaft to the mixer when the mixer is placed on the drive shaft in its second position. Such a second engagement section is preferably a distinct section located between the engagement section and the front end of the mixer.

In a preferred embodiment of the invention the mixer comprises a mixing rotor having a front end and a rear end, the rear end of the mixing rotor extending from the rear end of the mixer and comprising the engagement section for engagement with the mating engagement section of the drive shaft. Preferably the rear end of the mixing rotor is adapted to plug into a socket arranged on the drive shaft of the device according to the invention when the mixer is placed on the drive shaft, preferably when it is placed on the drive shaft in its second position.

According to a another aspect of the present invention a system for mixing and dispensing dental impression material is provided, comprising a mixer and a device, wherein one of the mixer and the device corresponds to an embodiment according to the invention.

Another aspect of the invention provides a method of mounting a mixer on a drive shaft of a device according to the invention, comprising the steps of:
 i) placing the mixer on the drive shaft in its first position;
 ii) aligning the mixer with an outlet of the device;
 iii) placing the mixer on the drive shaft in its second position by advancing it further along the drive shaft axis.

In still another aspect of the invention a kit is provided comprising a device according to the invention and a plurality of mixers. The kit preferably comprises at lest one improved device according to the invention and one or more mixers as available under the designation 3M™ ESPET Penta™ Mixing Tips from the 3M ESPE Company of Seefeld, Germany. Alternatively a kit is provided comprising a device as available under the designation 3M™ ESPE™ Penta™ Mixing Tips from the 3M ESPE Company of Seefeld, Germany and a plurality of improved mixers according to the invention.

The present invention is advantageous because it allows for easy and fast coupling of a mixer to a device for mixing and dispensing dental impression material. Further it reduces the potential of incorrect coupling of the mixer to the drive shaft and therefore helps ensuring that the torque required for mixing can be transmitted from the drive shaft to the mixer.

The guiding section can also be used to align the mixer coaxially to the mixing shaft during use. In this case the guiding section of the drive shaft fits with a blind hole arranged in the mixer adjacent to the engagement section. This prevents the shaft to unintentionally move out of the mixer in an axial direction during mixing. Such a gradually axial movement is an effect that generally may occur when a rotating shaft engages an axially disaligned borehole or bearing for torque transmission.

The invention further provides for transmission of high torques between the drive shaft and the mixer without making coupling of the mixer to the drive shaft complicated. It further provides the use of engagement sections providing transmission of higher torques relative to the prior art, for example the guiding section may comprise a star-shaped cross section. Such a configuration according to the invention still provides convenient coupling of the mixer to the drive shaft.

Further the invention is advantageous, as it allows the use of prior art mixers to be used with a device of the invention or prior art devices with a mixer of the invention.

It is pointed out that the discussion of the mating features of the drive shaft as well as of the mixer encompasses that either of them can be considered to be the male or the female part.

BRIEF DESCRIPTION OF THE DRAWINGS

Preferred embodiments of the invention are described in more detail below with reference to the attached drawings, which are by way of example only.

FIG. 1 is a perspective view of a device for mixing and dispensing dental impression material according to an embodiment of the invention;

FIG. 2a is a perspective view showing cross-sections of further details according to an embodiment of the device of the invention;

FIG. 2b is a magnified view on the details showed in FIG. 2a

DETAILED DESCRIPTION OF PREFERRED EMBODIMENTS

Figure 3A:
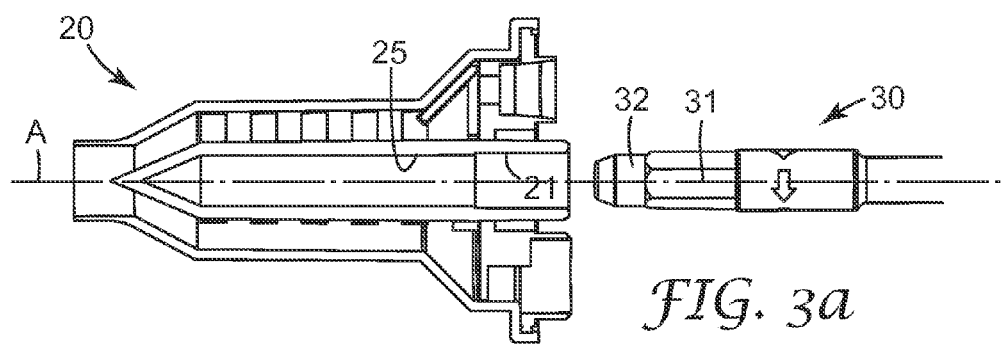
FIGS. 3a to 3c are cross-sectional views of the mixer and the drive shaft according to an embodiment of the invention, illustrating different stages of placement of the mixer on the drive shaft.

FIG. 1 is a perspective view of the mixing and dispensing device according to an embodiment of the invention. The device 1 receives a cartridge 10 comprising material chambers 11, 12 for storing of two components of a dental impression material. Preferably the cartridge 10 is exchangeable, e.g. it can be removed from the device and replaced by another cartridge of a similar configuration. This permits a user to change materials easily, and makes the device convenient to use with different dental materials.

As can be seen from FIGS. 2a and 2b, a mixer 20 is placed on a drive shaft 30, and mixer inlets 23, 24 are connected to respective outlets 13, 14 of the material chambers 11, 12. The mixer is secured against unintentional detachment by a locking lever 15 (shown in FIG. 1). The device further comprises plungers 51, 52 which are adapted to be displaced into the cartridge 10 in order to expel the dental material from the material chambers 11, 12 via the outlets 13, 14 into the mixer 20. In one embodiment of the invention, the dental material is stored in foil bags forming the material chambers (not shown), wherein the foil bags carry a rigid cap comprising the outlets. The foil bags are accommodated within channels of the cartridge. The plungers at their front end (which is the end facing the cartridge/material chambers) may comprise pressing members that are part of or connected to the plungers. Such pressing members may be in the form of pressing plates, pistons or the like, and preferably have cross-sections generally corresponding in size and shape to the channels of the cartridge. Preferably such pressing members are adapted to fit snugly into the channels of the cartridge. Alternatively or additionally, additional pressing members are displaceably accommodated in the channels of the cartridge, and preferably provide sealing with them. In this case the channels of the cartridge may form the material chambers for storing the dental material.

Figure 3B:
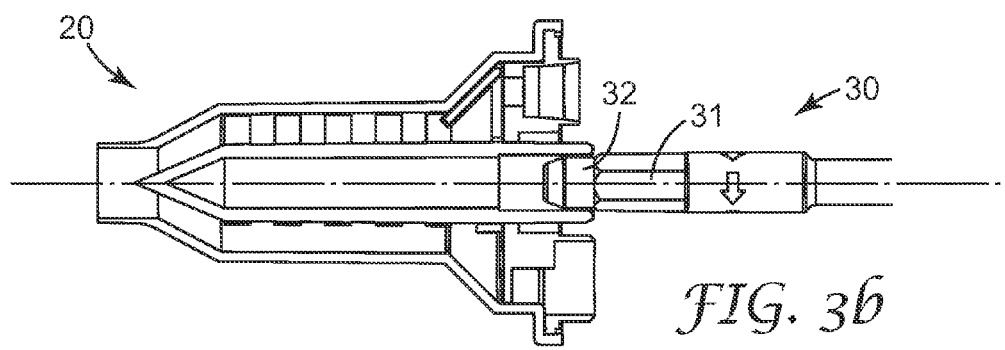
Figure 3C:
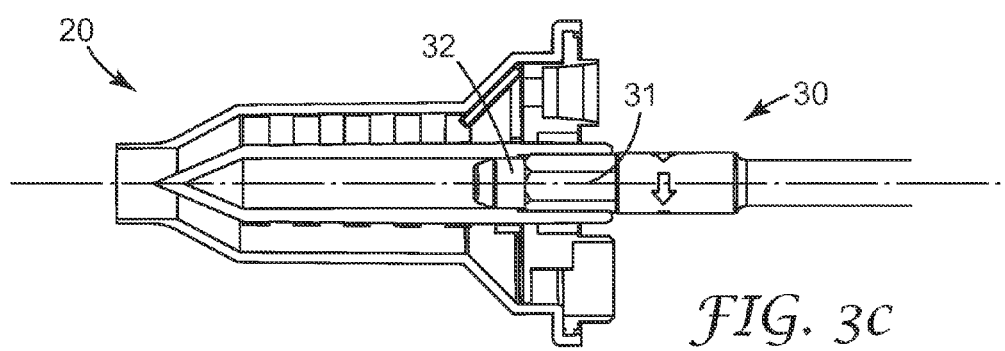

FIG. 3a to 3c are cross-sectional views of the mixer and the drive shaft, illustrating different stages of placement of the mixer on the drive shaft according to an embodiment of the invention. The drive shaft 30 comprises an engagement section 31 and a guiding section 32. The guiding section 32 of this embodiment has a cylindrical and an adjacent conical section, as illustrated. The mixer 20 is shown in FIG. 3a when it is separated from the drive shaft 30. As shown, the mixer 20 comprises a blind hole 25 and an engagement section 21. The engagement section 21 of the mixer 20 may extend along the whole length of the blind hole 25, or only along a part of it as shown. The engagement section 21 of the mixer 20 in the Figures is shown as a cylindrical hole, however the invention encompasses structures having different cross-sectional shapes, for example those shown in FIG. 5. Preferably the engagement section 21 of the mixer 20 has a hexagonal cross-section for mating with a hexagonal engagement section 31 of a drive shaft 30 as illustrated at the drive shaft 30. Preferably, the diameter of the blind hole 25 is equal or less than the diameter between the opposed flat sides of the hexagonal engagement section 31 in order to enable manufacturing by injection molding, and optionally to provide a stop at the transition between the engagement section 31 and the blind hole 25, to prevent the engagement section of the drive shaft to enter the blind hole.

In an alternative embodiment (not shown), the blind hole may have a diameter substantially smaller than the smallest dimension of the engagement section of the mixer. In this case, the guiding section of the drive shaft would preferably have a diameter substantially corresponding to the diameter of the blind hole, but a greater length than the engagement section of the mixer so as to be matable with the blind hole for guiding, instead of with the engagement section.

FIG. 3b shows the mixer 20 being placed on the guiding section 32 of the drive shaft 30, i.e., in the first position. The guiding section 32 of the drive shaft 30 is adapted to provide axial guidance with radial restraint within the engagement section 21 of the mixer 20, while the two remain rotatable around the rotation axis A relative to each other. This means that a user of the device can place the mixer 20 on the drive shaft in a first position without regard to the angular orientation of the engagement sections 31, 21 of the drive shaft 30 and the mixer 20 relative to each other, as required in the prior art. A guiding section as referred to can be for example a portion at the front end of the drive shaft having a generally circular shape as shown in FIGS. 3a to 3c. In this embodiment the guiding section 32 has a cylindrical section of a diameter equal or slightly less than the width between the flats of the hexagonal shape of the engagement section 21 of the mixer 20. To provide easy placement of the mixer 20 on the drive shaft 30, the guiding section at its front end preferably also comprises a conical section.

Once the mixer 20 is placed on the guiding section 32 of the drive shaft 30—the first position—it is easy to align and then connect the inlets 23, 24 of the mixer 20 to the outlets 13, 14 of the chambers 11, 12, because the mixer 20 can no longer move in two dimensions relative to the drive shaft. Thus, the inlets 23, 24 can be aligned to the outlets 13, 14 by just rotating the mixer to the appropriate angular orientation. This facilitates the accurate placement of the mixer 20 on the drive shaft 30, thus avoiding mistakes and saving time for the user of the device according to the invention.

As shown in FIG. 3c, once the appropriate angular orientation between the drive shaft and the mixer has been found, the mixer 20 can be pushed further onto the drive shaft 30. This mates the engagement section 31 of the drive shaft 30 with the engagement section 21 of the mixer 20, and the inlets 23, 24 with the outlets 13, 14 (not shown).

Although the inlets 23, 24 may already be aligned exactly with the outlets 13, 14 in some cases, the engagement sections 31, 21 may not match, because the angular orientation of their hexagonal shapes are randomly positioned relative to each other. This may happen because the engagement section of the mixer is arranged at a part which is rotatable relative to the inlets of the mixer and therefore has a random angular orientation relative to them. In cases the angular orientation of the engagement sections 31, 21 relative to each other do not match, the engagement sections are hindered to mate with one another when the mixer 20 is pushed onto the drive shaft. For this reason the drive shaft 30 is axially movable against a spring, thus allowing the drive shaft to be displaced backwards (to the right, in FIGS. 3a-3c), and causing the engagement sections 31, 21 to remain temporarily disengaged. In other words the mixer 20 with its inlets 23, 24 may be connected to the outlets 33, 34 while the engagement sections 21, 31 are still temporarily disengaged. In such a case mating of the engagement sections 31, 21 happens automatically as soon as the device is activated and the drive shaft starts rotating, because the drive shaft will be pushed forward by the spring and pop into place as soon as the angular orientation of the engagement sections 31, 21 match.

Figures 4A, 4B, 4C:
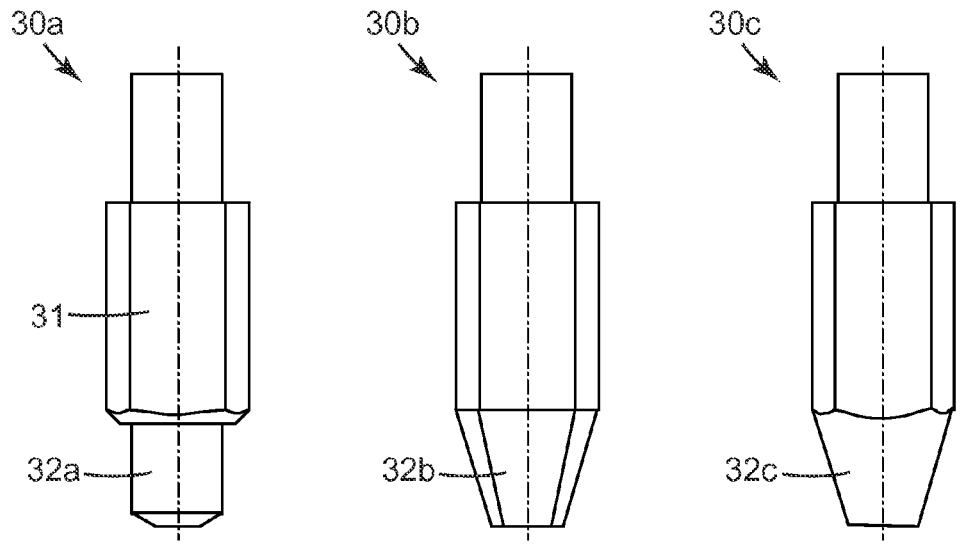
FIGS. 4a to 4c are schematic views of the front end of the drive shaft according to different embodiments of the invention.

FIGS. 4a to 4c show optional embodiments of the drive shaft 30a to 30c, respectively, with hexagonal engagement sections 31 and different guiding sections 32a to 32c, respectively. The guiding section 32a of FIG. 4a is similar to the guiding section 32 of FIGS. 3a to 3c having a circular cross-section, but it has a substantially smaller diameter relative to the diameter between the flats of the hexagonal shape of the engagement member 31. As illustrated, a further conical section or chamfered radial edge is arranged between the guiding section 32a and the engagement section 31 to facilitate mating of the engagement sections 31 of the drive shaft 30a and engagement section 21 of the mixer 20. In FIG. 4b, the guiding section 32b has a generally hexagonal cross-sectional shape but is tapered toward the front end of the drive shaft 30b. In FIG. 4c, the guiding section 32c has a generally conical shape.

Figure 5:
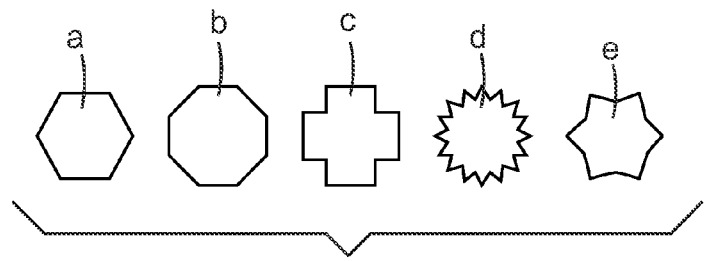
FIG. 5 shows different cross-sectional shapes for the engagement sections and/or the guiding sections of the drive shaft and/or of the mixer according to further embodiments of the invention.

FIG. 5 shows different cross-sectional shapes for the guiding and/or the engagement sections of the drive shaft and/or the mixer according to further embodiments of the invention. The shapes (labeled (a) to (e) are: (a) a hexagon, (b) an octagon, (c) a cross, (d) a first star having a plurality of points, and (e) a second star having less points relative to shape (d).

Figures 6A, 6B:
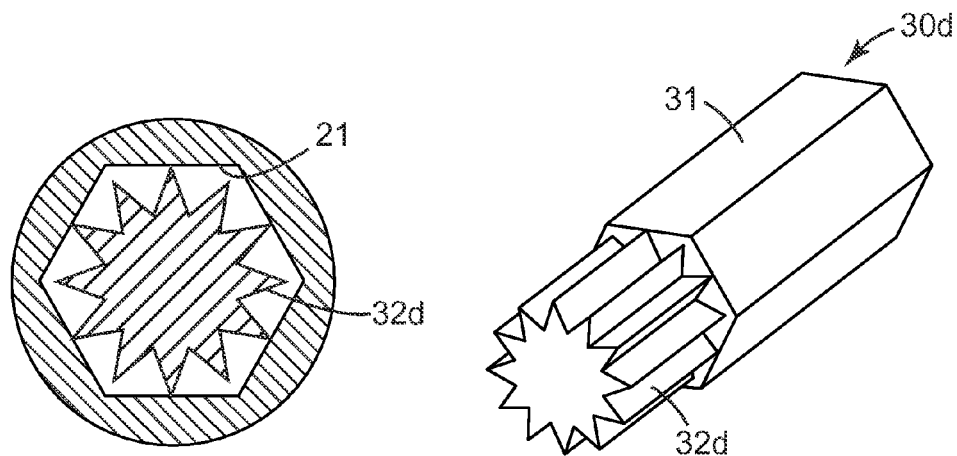
FIG. 6a is a cross-sectional view of a star-shaped guiding section of the drive shaft associated with a hexagonal engagement section of the mixer according to an embodiment of the invention.
FIG. 6b shows the drive shaft of FIG. 6a having a hexagonal engagement section and a star-shaped guiding section.

FIG. 6a illustrates a cross-sectional view of a guiding section 32d associated with a hexagonal engagement section 21 of the mixer. As can be seen, although the guiding section 32d has a star shaped cross-section, it guides the hexagonal engagement section 21 axially but restricts radial movement and still allows rotation of both sections relative to each other. FIG. 6b shows a corresponding drive shaft 30d according to an alternative embodiment of the invention, with the guiding section 32d and a hexagonal engagement section 31. A guiding section shaped in that manner provides for axial guiding with radial restraint of an engagement section of a mixer when the mixer is placed on the drive shaft in its first position. Furthermore a guiding section as shown can serve as a second engagement section of the drive shaft when engaging with an optional second engagement section of the mixer, i.e. when the mixer is placed on the drive shaft in its second position the engagement sections 31 and 21 engage with one another, and the guiding section 32d engages with a second engaging section of the mixer (not shown).

In such an embodiment the guiding section 32d is preferably shorter than the length of the engagement section 21 of the mixer. Thus, during placement of the mixer on the drive shaft and movement of the two from the first to the second position, the engagement sections first engage and establish an angular orientation appropriate for mating of the second engagement sections. This is of advantage because compared to the star shape the hexagon provides a lower degree of freedom for the angular orientation of the parts to be mated relative to each other. This means that the star shape can be designed to mate in any of the 6 possible angular orientations the hexagon allows. Thus, if first the hexagonal shapes are at least partially mated the star shapes will fit in any of the 6 angular positions, which can be achieved by making the star shaped guiding section shorter then the engagement section of the mixer.

In contrast, the star shape would allow for more than 6 possibilities for the angular orientation. This means, that in case the star shaped sections would be mated first, there are some angular orientations which would not allow for subsequently mating the hexagonal shapes. As a consequence a user would have to find an angular orientation by trial and error allowing for mating of both structures, which is not desirable.

Figure 7:
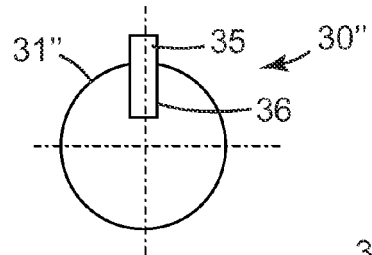
FIG. 7 is a schematic view on a front of an engagement section comprising a spline, according to another embodiment of the invention.

FIG. 7 shows an engagement section 31" of a drive shaft 30" having a spline 35 that fits within a keyway 36 formed in the drive shaft. The present invention also includes a drive shaft having multiple splines, as well as embodiments in which each spline is a separate or integral part of the drive shaft.

Figure 8:
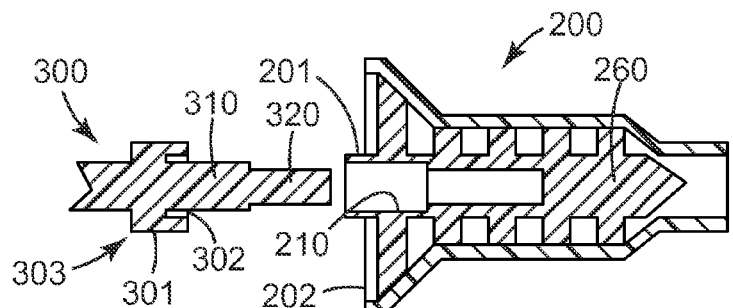
FIG. 8 is a cross-sectional view of a mixer and an embodiment of the drive shaft comprising a socket according to an alternative embodiment of the invention.

FIG. 8 shows a drive shaft 300 and a mixer 200 according to another embodiment of the invention. The drive shaft 300 comprises, from the front end towards the rear end of the drive shaft 300: a guiding section 320, an engagement section 310 and a flange 301. The flange 301 comprises a recess 302 extending axially from the front surface into the flange 301, both structures forming a socket 303. The mixer 200 comprises a mixing rotor 260 having a rear end 201 extending from the rear end 202 of the mixer 200. When the mixer is placed on the drive shaft in its second position the engagement section 310 of the drive shaft 300 engages with the mating engagement section 210 of the mixer 200, and the rear end 201 of the mixing rotor 260 is inserted in the recess 302 of the drive shaft 300. In other words, the rear end 201 of the mixing rotor is plugged into the socket 302 of the drive shaft 300. As a result the rear end 201 of the mixing rotor, which is often made of plastic, is reinforced by the socket 303 of the drive shaft 300, which is commonly made of metal. This enables the maximum torque transmittable from the drive shaft 300 to the mixing rotor 260 to be increased, because deformation of the engagement section 210, due to forces transmitted by the engagement section 310 of the drive shaft 300, is reduced.

Figure 9A:
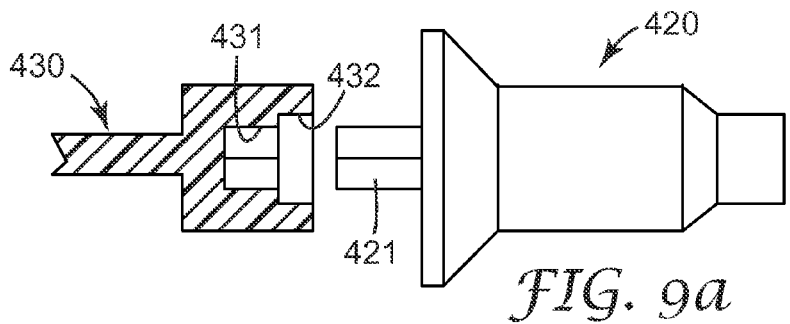
FIGS. 9a to 9c show a drive shaft comprising the female part and a mixer comprising the male part of the mating of both according to a further embodiment of the invention, at different stages of placement of the mixer on the drive shaft.
Figure 9B:
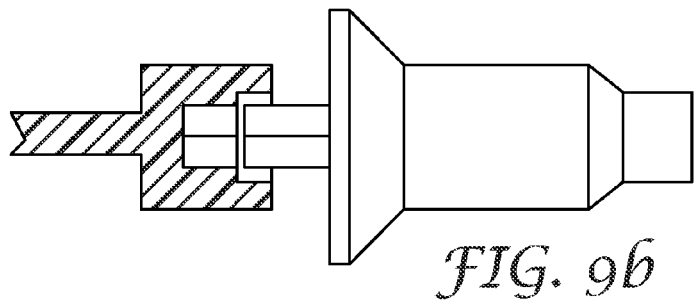
Figure 9C:
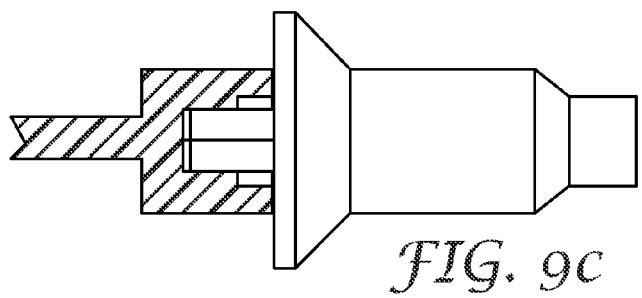

FIGS. 9a to 9c show schematic views of alternative embodiments of the mixer and the drive shaft illustrating different stages of placement of the mixer on the drive shaft. The mixer 420 is shown in FIG. 9a when it is separated from the drive shaft 430. In contrast to the embodiments shown in FIGS. 3a to 3c, the mixer 420 comprises a male engagement section 421 and the drive shaft 430 comprises female engagement and guiding sections 431, 432 respectively. The engagement section 421 of the mixer 420 has a hexagonal cross-section for mating with a hexagonal engagement section 431 of a drive shaft 430. However, other cross-sectional shapes as discussed above are encompassed.

FIG. 9b shows the mixer 420 being placed on the guiding section 432 of the drive shaft 430. In this embodiment the guiding section 432 has a cylindrical section having a diameter equal to or slightly greater than the width between the flats of the hexagonal shape of the engagement section 421 of the mixer 420. To provide easy placement of the mixer 420 on the drive shaft 430 the guiding section at its front end preferably comprises also a conical section (not shown).

As shown in FIG. 9c, the mixer 420 is pushed further onto the drive shaft 430 (which may be spring-loaded as described above), so as to mate the engagement section 431 of the drive shaft with the engagement section 421 of the mixer. This embodiment, may be considered to be the reverse of the embodiments described previously, in that the male and female portions of the various components are generally reversed.

Figure 10:
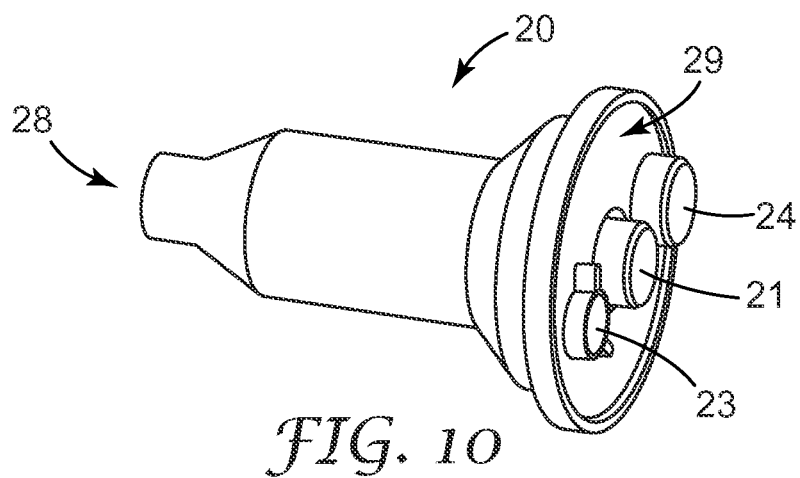
FIG. 10 is a perspective view on a mixer which can be used with a device according to the invention.

FIG. 10 shows a mixer of the present invention, including the material inlets. The mixer 20 has a front or dispensing end 28 and a rear end 29. Further the mixer comprises inlets 23, 24 and an engagement section 21.

Figure 11:
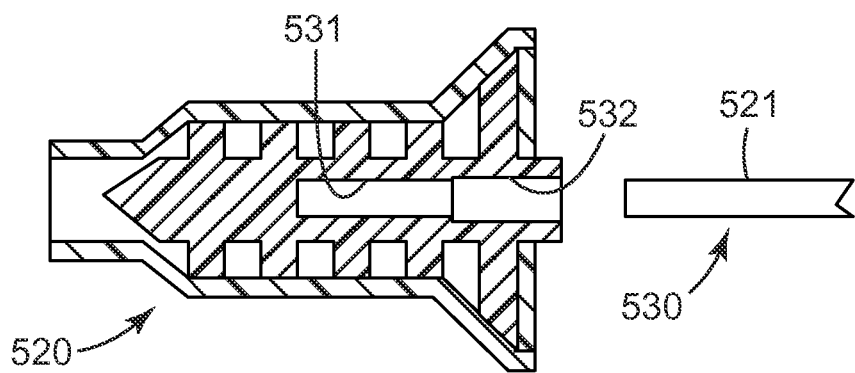
FIG. 11 shows a schematic view of a mixer according to the invention having a guiding section and an engagement section, and a drive shaft with an engagement section without a guiding section.

FIG. 11 shows a schematic view of a mixer 520 having a guiding section 532 and an engagement section 531 and a drive shaft 530 with an engagement section 521 without a guiding section. For simplicity, the material connections associated with the mixer and the device are not shown. The guiding section of the mixer 532 may be of cylindrical and/or conical shape. Optionally the guiding section 532 may comprise a non-circular shape, for example as mentioned for the non-circular shapes of the guiding section of the drive shaft above. In this case the drive shaft may comprise a second engagement section for engagement with the guiding section of the mixer when the mixer is placed on the drive shaft in its second position.

It is pointed out that generally all features described for the drive shaft may be considered as features of the mixer, and vice versa, as illustrated in the embodiments shown in FIGS. 9a to 9c in comparison to other embodiments. Furthermore combinations of features of the drive shaft and the mixer are explicitly encompassed.

The present invention has now been described with reference to several embodiments thereof. It will be apparent to those skilled in the art that many changes can be made in the embodiments described without departing from the scope of the present invention. Thus the scope of the present invention should not be limited to the structures described in this application, but only by structures described by the language of the claims and the equivalents of those structures.

The invention claimed is:

1. A system for mixing and dispensing dental impression material, comprising
a mixer and
a device connectable with the mixer the device comprising
a drive shaft for driving the mixer;
wherein the drive shaft has a front end comprising a guiding section and an engagement section for engagement with an engagement section of the mixer,
wherein the guiding section of the drive shaft has a generally circular cross-section and the engagement section of the drive shaft comprises a non-circular cross-section, and
wherein the drive shaft comprises a female part engagement section corresponding to a male part engagement section of the mixer.

2. A method of mounting a mixer on a drive shaft of a system as defined in claim 1, comprising:
i) placing the mixer on the drive shaft in a first position;
ii) connecting the mixer with an outlet of the device; and
iii) placing the mixer on the drive shaft in a second position.

3. A kit comprising a system as defined in claim 1, and a plurality of additional mixers.

4. The system of claim 1, wherein the mixer is placeable on the drive shaft in a first and a second position,
wherein in the first position the guiding section of the drive shaft is mated with the engagement section of the mixer, but the engagement section of the drive shaft is not engaged with the engagement section of the mixer, and
in the second position the engagement section of the drive shaft is engaged with the engagement section of the mixer.

5. The system of claim 4, wherein the guiding section is adapted such that, when the mixer is placed on the drive shaft in the first position the guiding section is freely rotatable around the longitudinal axis of the guiding section relative to the engagement section of the mixer.

6. The system of claim 5, wherein the guiding section of the drive shaft and the engagement section of the mixer are connected in the first position, in such a manner that the connection allows free rotatability of one relative to the other.

7. The system of claim 1, wherein the guiding section of the drive shaft comprises a conical shape.

8. The system of claim 1, wherein the engagement section of the drive shaft comprises a spline.

9. The system of claim 1, wherein the engagement section of the drive shaft has a generally polygon-shaped cross-section.

10. A system for mixing and dispensing dental impression material, comprising
a mixer,
a device connectable with the mixer, the device comprising
a drive shaft,
wherein the drive shaft has a front end comprising a guiding section and an engagement section for engagement with an engagement section of the mixer, and
wherein the guiding section of the drive shaft has a generally circular cross-section and the engagement section of the drive shaft comprises a non-circular cross-section, and a chamber,
wherein the chamber opens into an outlet which is connectable with a corresponding inlet of the mixer, when the engagement section of the drive shaft is engaged with the engagement section of the mixer.

11. The system of claim 10, wherein the outlet is at least partially connectable with the corresponding inlet of the mixer when the guiding section of the drive shaft is mated with the engagement section of the mixer, but the engagement section of the drive shaft is not engaged with the engagement section of the mixer.

12. The system of claim 11, further comprising a plunger displaced into the chamber for expelling the at least one component of the dental impression material from the chamber into the mixer.

13. A system for mixing and dispensing dental impression material, comprising
   a mixer, wherein the mixer has a front end and a rear end, the rear end comprising a guiding section and an engagement section, and
   a device connectable with the mixer, the device comprising a drive shaft;
   wherein the drive shaft has a front end comprising a guiding section and an engagement section for engagement with the engagement section of the mixer,
   wherein the guiding section of the drive shaft has a generally circular cross-section and the engagement section of the drive shaft comprises a non-circular cross-section,
   wherein the mixer comprises a mixing rotor having a front end and a rear end, the rear end of the mixing rotor extending from the rear end of the mixer and comprising the engagement section of the mixer for engagement with the engagement section of the drive shaft, and
   wherein the rear end of the mixing rotor is adapted to plug into a socket of the drive shaft when the mixer is placed on the drive shaft.

14. The system of claim 13, wherein the cross-section of the engagement section of the mixer has a polygon shape.

15. The system of claim 13, wherein the cross-section of the engagement section of the mixer has a shape selected from a square, a rectangle, a hexagon, a cross and a star.

16. The system of claim 13, wherein the engagement section of the mixer has a cross-section generally corresponding to the cross-sectional shape of the engagement section of the drive shaft.

17. The system of claim 13, wherein the engagement section of the mixer has a substantially different cross-section relative to the cross-sectional shape of the engagement section of the drive shaft.

* * * * *

UNITED STATES PATENT AND TRADEMARK OFFICE
CERTIFICATE OF CORRECTION

| | | |
|---|---|---|
| PATENT NO. | : 8,579,497 B2 | Page 1 of 1 |
| APPLICATION NO. | : 12/281999 | |
| DATED | : November 12, 2013 | |
| INVENTOR(S) | : Manfred Harre et al. | |

It is certified that error appears in the above-identified patent and that said Letters Patent is hereby corrected as shown below:

On the Title Page, Item (54) and in the Specification, Column 1, Line 3, (Title), delete "METHOD" and insert -- A METHOD --, therefor.

On the Title Page, Item (87) Column 1 (PCT Publication Date) - delete "Sep. 26, 2007" and insert -- Sep. 20, 2007 --, therefor.

In the Specification

Column 6

Line 27 (Approx.), - delete "at lest" and insert -- at least --, therefor.

Column 6

Line 29, - delete "ESPET" and insert -- ESPE™ --, therefor.

Column 7

Lines 7-8, - delete "FIG. 2a" and insert -- FIG. 2a; --, therefor.

Column 10

Line 25, - delete "shorter then" and insert -- shorter than --, therefor.

Signed and Sealed this
First Day of July, 2014

Michelle K. Lee
*Deputy Director of the United States Patent and Trademark Office*